US006927395B2

(12) United States Patent
Koops et al.

(10) Patent No.: US 6,927,395 B2
(45) Date of Patent: Aug. 9, 2005

(54) GAMMA CAMERA COLLISION AVOIDANCE

(75) Inventors: Ronald Koops, Castro Valley, CA (US);
Pierre Patino, Aptos, CA (US); Mark DeSilets, San Jose, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 228 days.

(21) Appl. No.: 10/172,618

(22) Filed: Jun. 14, 2002

(65) Prior Publication Data

US 2003/0230724 A1 Dec. 18, 2003

(51) Int. Cl.[7] ............................................. G01T 1/164
(52) U.S. Cl. .................................................. 250/363.08
(58) Field of Search ................................... 250/363.08

(56) References Cited

U.S. PATENT DOCUMENTS

| 5,376,796 | A |   | 12/1994 | Chan et al. |         |
|-----------|---|---|---------|-------------|---------|
| 5,485,502 | A |   | 1/1996  | Hinton et al. |       |
| 5,677,535 | A | * | 10/1997 | Stephan ................ | 250/363.02 |
| 5,878,112 | A |   | 3/1999  | Koertge |             |
| 6,150,662 | A | * | 11/2000 | Hug et al. ............ | 250/363.08 |
| 6,678,582 | B2 | * | 1/2004 | Waled ....................... | 700/245 |
| 2003/0112281 | A1 | * | 6/2003 | Sriram et al. ............... | 345/958 |

FOREIGN PATENT DOCUMENTS

| DE | 3604955 A1 | 2/1986 |
| GB | 1 362 678 | 8/1974 |

OTHER PUBLICATIONS

M. Lin, D. Manocha, J. Cohen, and S. Gottschalk. "Collision Detection: Algorithms and Applications." in: Algorithms for Robot Motion and Manipulation, pp. 129–142, eds. Jean–Paul Laumond and M. Overmars, A.K. Peters (Invited Submission), 1996.*

J. Cohen, M. Lin, D. Manocha, and K. Ponamgi. "I–COL-LIDE: An Interactive and Exact Collision Detection System for Large–Scaled Environments." Proc. ACM Symposium on Interactive 3D Graphics, pp. 189–196, 1995.*

Thomas C. Hudson et al., "V–COLLIDE: Accelerated Collision Detection for VRML." VRML '97, Proceedings of the Second Symposium on Virtual Reality Modeling Language, Feb. 24–26, 1997, Monterey, California, USA, pp. 117–124.*

* cited by examiner

*Primary Examiner*—Constantine Hannaher

(57) ABSTRACT

A method of avoiding collisions with components of medical diagnostic imaging system includes defining a plurality of imaging system components as wire frame representations having vertices. The objects in the imaging system are defined in a common coordinate system using transform matrices for the imaging system components. An operator initiates movement of the imaging system components and position and motion input signals are provided to a controller. The transform matrices for imaging system components are updated and a final transform is computed in response to the input signals for the imaging system components, the final transform indicative of a position of imaging system components at a predetermined time interval. The final transform is applied to the wire frame representation generating a new position for the wire frame and a determination is made as to whether a collision is occurring between any of the plurality of imaging system components using the new wire frame positions.

17 Claims, 5 Drawing Sheets

GAMMA CAMERA COLLISION AVOIDANCE

BACKGROUND

The present invention relates to medical diagnostic imaging systems and is particularly related to a method and apparatus for real time determination and control for preventing collisions between members of the imaging system and objects within the range of motion of the imaging system components.

Conventional nuclear medicine imaging systems include one or more detectors supported by a gantry. The gantry typically provides mechanical movement of the detectors to allow the detectors to be positioned in various locations and orientations around the patient's body during the acquisition of image data. Hence, image data can be acquired from various different angles about the patient. In conventional imaging systems, the gantry is a floor-mounted structure. In some systems, the gantry includes one or more closed, ring-shaped supports, to which the detectors are mounted. The detectors are adjustable radially and move around an examination region in a circular path defined by the rings. The patient is placed within or next to the closed rings, and the rings are rotated with a motor to position the detectors appropriately about the patient. Particularly during operator controlled set up of these imaging systems in preparation for an imaging sequence, some components of the imaging system can collide with one another or other structures in the room and cause damage to the imaging system components. For example, collisions can occur between the detectors, collimators, patient support, floor, gantry ring, transmission line sources and room objects such as cabinets, doors, sinks as well as other known fixtures and objects.

In other recent nuclear diagnostic imaging systems, an overhead gantry structure provides detector supports having translatable, rotating and extendable articulated arms that provides three-axis linear and rotary detector motion. The overhead gantry suspends the detectors from overhead thereby providing easier access for bed-ridden, wheel chair bound and otherwise less mobile patients. In addition, the overhead gantry configuration provides greater flexibility to image patients in a variety of positions previously not available.

However, while such systems have certainly significantly improved many aspects of diagnostic imaging, the improved range of motion of the imaging system components throughout the imaging suite permits the system components to potentially come in contact with other components and objects within the room. Each imaging suite can have different fixtures and objects which can collide with the imaging system. In addition, changes in the number or location of objects within the imaging suite presents a changing environment that can result in collisions and damage to the imaging system. Collisions of system components can result in (i) costly damage to the system, (ii) down time and lost revenue during repair and (iii) disrupted imaging of a patient such that the imaging sequence must be run again at a later time, thereby subjecting the patient to additional doses of radio-pharmaceutical imaging agents.

SUMMARY OF THE INVENTION

The present invention is directed to a method and apparatus that satisfies the need to provide an imaging system which performs real time collision analysis and avoidance for the components of the imaging system. The system reduces collisions between system components and objects located within the imaging suite that can damage the system. An apparatus in accordance with one embodiment applying principles of the present invention includes a gantry, a detector support operatively connected to the gantry and a detector operatively connected to the detector support. An imaging controller controls operation of the detector and detector support. Included in the controller, an object model reader dataset stores data related to attributes for the surfaces of the gantry, detector and detector support. A motion compute dataset defines the kinematic relationship, with transform matrices, between the gantry, the detector support and the detector. Objects within the range of motion of the gantry, detector and detector support as defined in the kinematic relationships are modeled in the object model dataset. A collision detect processor in the controller performs real time collision analysis between objects in the model reader dataset.

A method in accordance with principles of the present invention includes the steps defining a plurality of imaging system components as wire frame representations having vertices. The objects in the imaging system are defined in a common coordinate system using transform matrices for the imaging system components. An operator initiates movement of the imaging system components and position and motion input signals are provided to a controller. The transform matrices for imaging system components are updated and a final transform is computed in response to the input signals for the imaging system components, the final transform indicative of a position of imaging system components at a predetermined time interval. The final transform is applied to the wire frame representation generating a new position for the wire frame and a determination is made as to whether a collision is occurring between any of the plurality of imaging system components using the new wire frame positions.

An apparatus and method applying principles of the present invention provides the foregoing and other features hereinafter described and particularly pointed out in the claims. The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

BRIEF DESCRIPTION OF THE DRAWINGS

The foregoing and other features and advantages of the present invention will become apparent to those skilled in the art to which the present invention relates upon consideration of the following detailed description of a method and apparatus applying aspects of the present invention with reference to the accompanying drawings, wherein.

DETAILED DESCRIPTION

Figure 1:
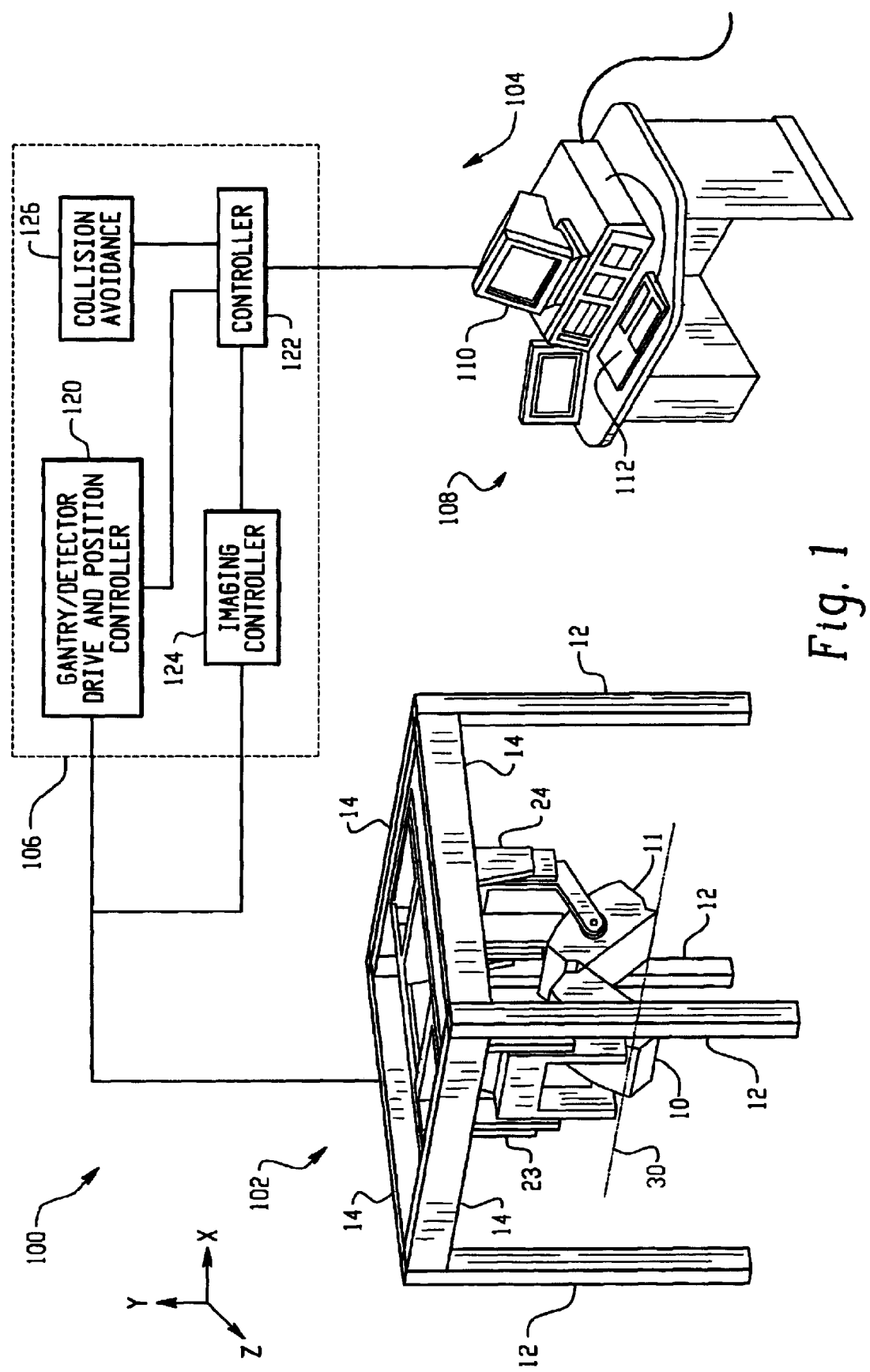
FIG. 1 is a schematic representation of a diagnostic imaging system in accordance with principles of the present invention.

With reference to FIG. 1, a nuclear medicine imaging system 100 has an overhead gantry 102 and control and image processing system 104. The control and image processing system 104 includes a gamma camera control processor 106, an operator interface 108, a display system 110 and input device such as a keyboard 112, touch screen, trackball, joystick or other suitable operator input interface. The operator interface also provides for notifying the operator of alarms, system and component operating status and manual system control features.

The control and image processing system 104 coordinates the operation of the scanner 100. All of the control and imaging processing functions in the illustrated components and systems can be performed by known computer based systems having an operable complement of component systems such as suitable processors, memory and storage, input, output and data communications capabilities as well as remotely located systems in suitable data communication with one another.

The gamma camera control processor 106 includes all appropriate computer hardware and software components to operate within a diagnostic imaging system. A gantry detector drive and position controller 120 is controllably connected to various sensors and drive mechanisms used for tracking, moving and positioning the detector heads 10, 11. The gantry drive controller 120 is controllably connected to the system controller 122 which coordinates between the various control and system functions of the imaging system as well as the operator interface 108. The system controller 122 is operatively connected to an imaging controller 124, suitably connected to the detector 10, 11, which performs functions related to image processing such as providing scan protocols and detector positioning sequences, data acquisition, reconstruction, storage, registration, fusion or other functions related to processing of image data and providing human readable display of the acquired image data. A collision avoidance function 126 is operatively connected to the system controller 122 to perform ongoing collision avoidance analysis for components of the imaging system.

The gantry 102 is used to support and provide for movement of two gamma ray detectors 10 and 11 for purposes of acquiring image data of a patient. During certain types of imaging studies, such as single photon emission computed tomography (SPECT), the detectors 10 and 11 are positioned at various different angular positions about a longitudinal axis 30, to acquire image data from different angles about the patient's body. The longitudinal axis 30 ordinarily passes through the patient's body lengthwise and for a particular imaging study may be the center of rotation of the detectors 10 and 11. Movement and configuration of the gantry 102 to position the detectors 10 and 11 are controlled by the control and processing computer system 104, as are the data acquisition and image reconstruction processes.

The overhead gantry 102 includes four members (beams) 14, which are connected at their ends to generally form the shape of a rectangle. The beams 14 are supported in horizontal orientations off the floor at the corners of the rectangle by vertical columns 12. The beams 14 are supported high enough off the floor so that a person can walk under them. Alternatively, the horizontal beams 14 may be mounted to the ceiling rather than supported from below.

The gantry includes two support arms 23 and 24 suspended downward from overhead positions. Support arm 23 supports detector 10, while support arm 24 supports detector 11. The support arms 23 and 24 allow detectors 10 and 11 to be moved in translation horizontally in both the x direction (perpendicular to the longitudinal axis 30) and the z direction (parallel to the longitudinal axis 30). In addition, the support arms 23 and 24 comprise suitable members to include prismatic joints such that each detector can perform a "telescoping" action, i.e., can extend or retract in the y direction. Hence, each detector is always suspended by its support arm from above the patient, even though the detector itself may at times be located below the patient during an imaging session.

As described below, the support arms 23, 24 include suitable revolute joints in which the relative angle between support segments can be changed. Further, in contrast with conventional ring-based systems, the paths of motion of the detectors are independent of each other.

Figure 2:
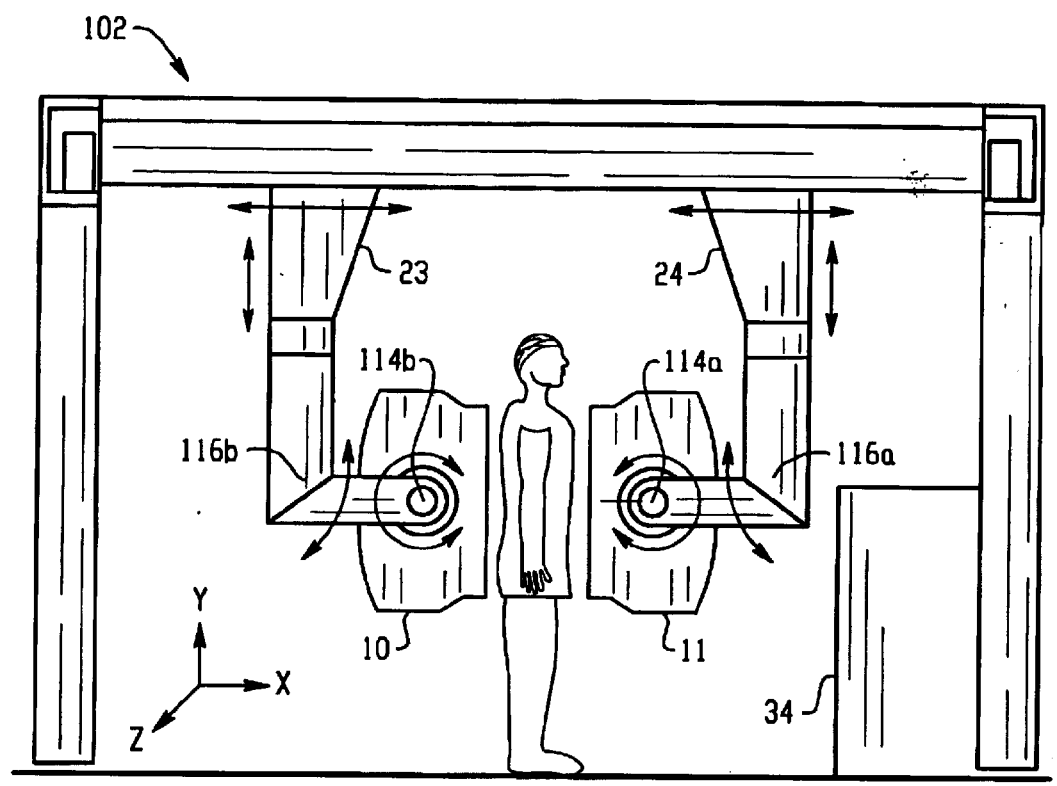
FIG. 2 is an illustration of an overhead gantry imaging system showing a configuration of the detector supports and types of motion for system components within an imaging suite.
Figure 3:
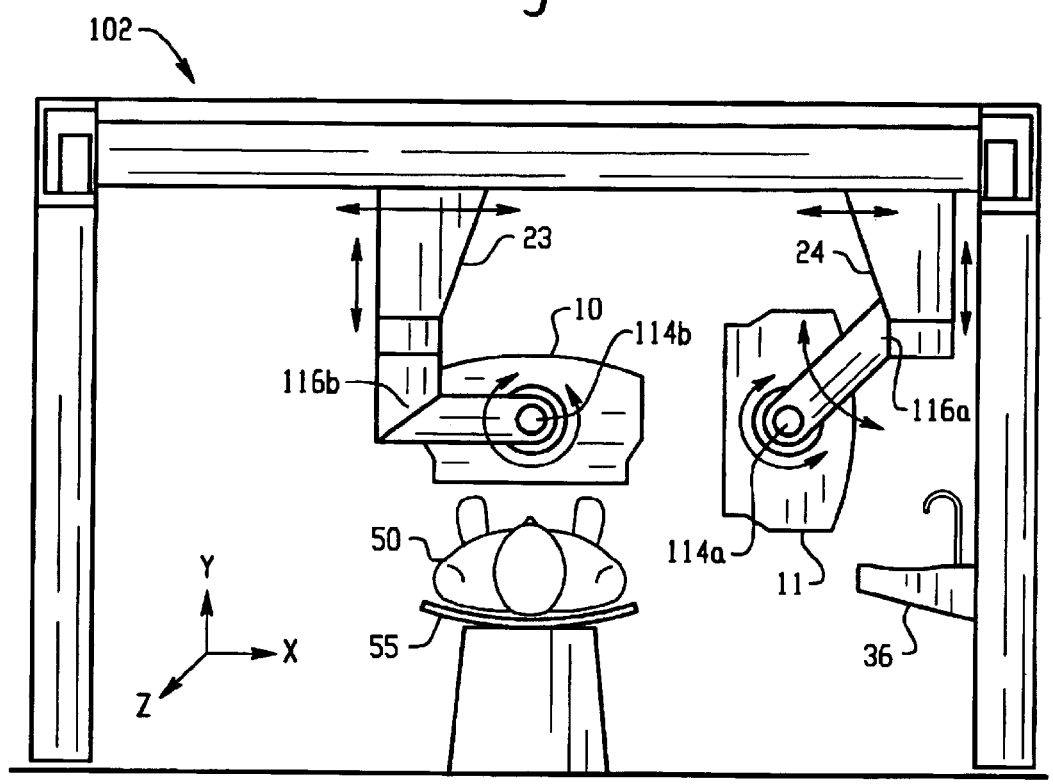
FIG. 3 is an illustration of an overhead gantry imaging system showing another configuration of the detector supports and types of motion for system components within an imaging suite.

It may be desirable for the beams 14 to have different lengths to conform the dimensions of the gantry 102 to the dimensions of the room in which it is to be located. Each of the vertical columns 12 can be located against or near a wall to provide greater access to the patient and to otherwise facilitate movement of attending personnel, life support systems, and other equipment. In addition, examples of objects within the imaging suite that can be involved in a collision with the imaging system objects include a cabinet 34 (FIG. 2) and a sink 36 (FIG. 3.)

As noted above, the overhead gantry 102 provides greater flexibility than conventional systems in positioning the detectors 10, 11. In FIGS. 1–3, the gantry 102 is a three dimensional Cartesian manipulator that has for each arm three prismatic joints for the x, y, and z axes which allow the end effector—a gamma ray detector in this case—to be positioned anywhere in the rectangular solid volume defined by those axes. FIGS. 2 and 3 illustrate the orientation of the principal axes with respect to a patient table 55, as well as the imaging suite and other objects within the space. In addition to the three Cartesian axes, the gantry 102 has a revolute joint 114a and 114b at the end of each arm for rotating the detector around the patient (i.e. about a line parallel to the x-axis). Additional revolute joints 116a and 116b can be included to provide greater flexibility in positioning the detectors 10, 11 within the imaging suite.

Figure 4:
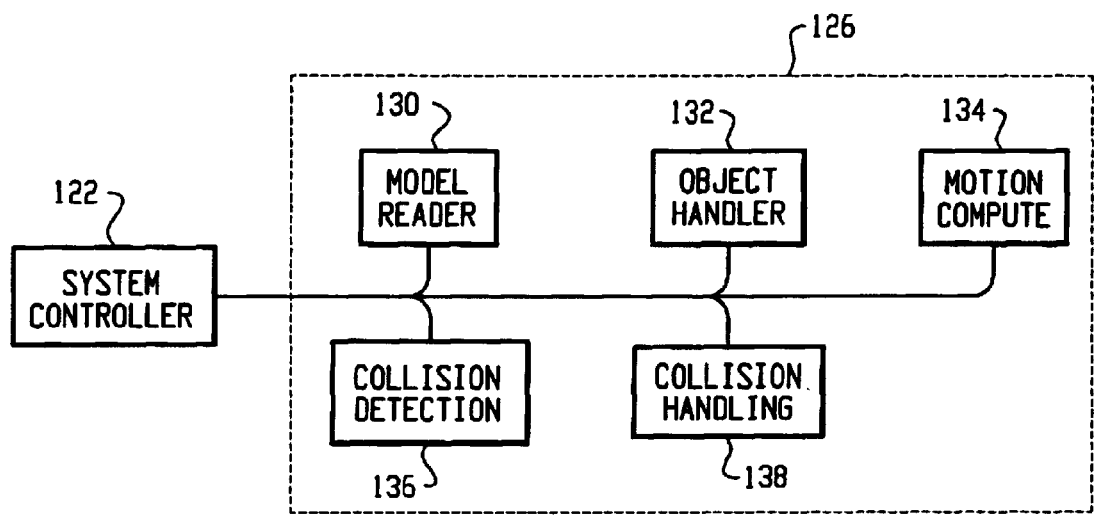
FIG. 4 is a block diagram illustrating an apparatus in accordance with principles of the present invention.

Turning now to FIG. 4, the collision avoidance function 126 monitors the motion of the objects in the gantry and imaging system and their positions relative to other movable and fixed objects to reduce the likelihood that imaging system components will collide with another object. The collision avoidance function 126 is particularly effective during operator handcontroller motions of the movable imaging system components. For example, the operator uses the operator interface 108 to place the detectors 10, 11 in their initial position near a patient to begin the data acquisition for an imaging scan. As the imaging system components are manipulated by the operator, potential collisions are checked real time by computing each component's lookahead position relative to other objects within the imaging suite.

A model reader 130 stores a three dimensional model for each object in a collision model file. The description of each object is from known physical dimensions and starting locations of the objects of the gantry system and imaging suite. Each object file can be formed from one or more geometric structures for each object. The objects are associated with links in the imaging system such as the detectors 10, 11, the support arms 23, 24, patient table 55.

For many objects in the imaging system, a polyhedra is sufficient to model the structure. Each object is first defined relative to a suitable reference frame by a wire frame in a three dimensional coordinate system. Each vertex at the intersection of the wire frame segments have an X, Y, and Z coordinate in the reference frame. New objects and site specific structures can be added to the model reader 130 by the operator using the user interface shown in FIG. 6 as described below. If desired, a buffer zone can be added to the object dimensions and coordinates to provide a collision avoidance process (CAP) thickness around the surface of the object. This may be 1 cm–5 cm larger than the object thereby providing earlier operator notification of a potential upcoming collision. Each surface of the object is further decomposed into a set of triangles for use as vertex triangle models of the objects suitable for use with the collision software described below.

An object handler 132 tracks which objects within the imaging suite and gantry system are currently active and interfaces with a collision detection function 136 to set up pairwise (object to object) collision testing. Depending on desired operation, some objects may be disabled or re-enabled. For example, only a single detector 10 and corresponding support arm 23 may be active for a given clinical imaging protocol. As such, the active detector may not have the range of motion to collide with the cabinet 36, which may be disabled for this particular imaging sequence. However, the next patient scanned may require both detectors 10, 11 to be active and the cabinet 34 is re-enabled and tracked by the object handler as an object to be checked for potential collision. In addition, different collimators have different shapes and, depending on the selected collimator, different attributes for the various collimators are stored in the model reader 130. Since different clinical imaging protocols may require different collimators (or no collimators at all), the object representing the collimator on a detector can be disabled as desired. In some instances, pairs of objects can be determined that they will never collide. For example, even if the patient table 55 can translate a patient during an imaging sequence, it may never be able to collide with the cabinet 34 or sink 36. As such, a collision comparison is not necessary at any time and the object handler tracks these relationships between objects to remove non-colliding pairs form collision detection tests. Eliminating potential collision objects and pairs improves computation time of the collision tests. In another example, components may be disabled or enabled if the system configuration or imaging suite is changed.

A motion compute function 134 computes motion of an object. The objects have velocity, position and rotation. For the objects to be compared for collision a common coordinate system is established using transform matrices to convert form one coordinate system to another. Each link or object within gantry system has its own relative location to its next attached link. Actuators, such as motors, are connected to the links for motion and to provide position signals to the controller. A given object may have a number of intermediate matrices to be used in obtaining a final transform matrix for an object relative to the common coordinate system. Multiplying the wireframe coordinates of an object by the final transform yields the new coordinates for the object's current location to be used by the collision algorithms for the collision determination below. The coefficients of the intermediate matrices are computed form the actuators that rotate and translate each object from the previous position to the current position. Some of the intermediate transform matrices may be shared by more than one object, thereby reducing required computation resources.

A motion compute function 134 computes motion of an object by adding a motion shift to the current position of the object. For example, in a relative positive motion;

[New Position]=[Current Position]+[Lookahead Delta]+[CAP Thickness]

and, for a relative negative motion;

[New Position]=[Current Position]−[Lookahead Delta]−[CAP Thickness]

where;
  current position is read from mapped object coordinates;
  lookahead delta is a trapezoidal velocity profile used to compute the amount of change in motion due to a lookahead time of 0.5 second;
  CAP Thickness is a buffer zone which can be uniform or alternatively uniquely applied to each axis of the object. Anticipated intrusion into the CAP thickness between objects from the collision testing will result in audible warnings and stop motion command to the gantry drive controller 120.

The desired collision distance describes the allowed proximity between objects before collision is detected. Although the size of the CAP thickness reflects the desired collision distance, the physical distance between objects is dependent on the ability of the internal collision avoidance model to represent the physical object. The model is typically larger than the object and will add some additional distance to the actual proximity performance. For example, in the case of the table, the vertical position of the table is known only to within +2.5/−0.5 cm (−1.5 cm spec.) due to table sag, or deformation. Since the table is modeled to include its full extent, a maximum deformation of 3 cm can add 3 cm to the minimum collision proximity between the table and other objects in the vertical direction.

Once the new position is computed, the objects in the model must be updated so that they are moved to the new locations. Each object has a current 4×4 transformation matrix to describe its position in space. The matrix is used to transform the object (its vertices) and compute the new location of the object for the next frame, i.e. for the next lookahead check. When the model file is first read in, all objects are assumed to be at a known starting axis position so that the motion can be computed relative to this reference position. The sequence of transformations is computed using translation and rotation matrices to come up with the total transformation matrix for each object.

A collision detection function 136 is conducted using algorithms once positions of the objects are updated. A suitable combination of collision algorithms/programs for use in the present invention include V-Collide and RAPID. Both programs are available from Ming Lin PhD., of the University of North Carolina at Chapel Hill. RAPID is a public domain package and the use of both programs is further described in *V-Collide: Accelerated Collision Detection for VRML*, VMRL Proceedings 1997, pp. 117–125, which is incorporated herein by reference.

In general, the V-Collide/RAPID algorithm computes a hierarchical tree of oriented bounding boxes (OBBs) to represent each object. Checks between bounding boxes are done at successive levels, progressing from testing with coarse approximations down to closer approximations. Specifically, a quick conservative approximation finds potentially colliding pairs of objects in the database using a sweep and prune algorithm such as an n-body algorithm. Then intersection testing is done using disjointedness tests between the OBBs which utilize theorems on separating planes/separating axes. If the two objects' OBBs are disjoint, then the objects do not intersect and do not collide.

If needed, triangle-triangle intersection tests are done at the final level of checking.

A collision handling function 138 notifies the rest of the system via the system controller 122 on the results of the collision tests. If no collision is detected, motion proceeds under normal operation. If a collision is detected, the collision avoidance function 126 sends a motion stop to each of the active axes. Continued motion in the direction of collision is inhibited while allowing the operator to back out of the collision by moving in the opposite direction. If, after finds an imminent collision, the user continues to press the button to move the stopped axes in the direction of collision, an audible beep or visual warning on the user interface is generated to notify the user.

Figure 5:
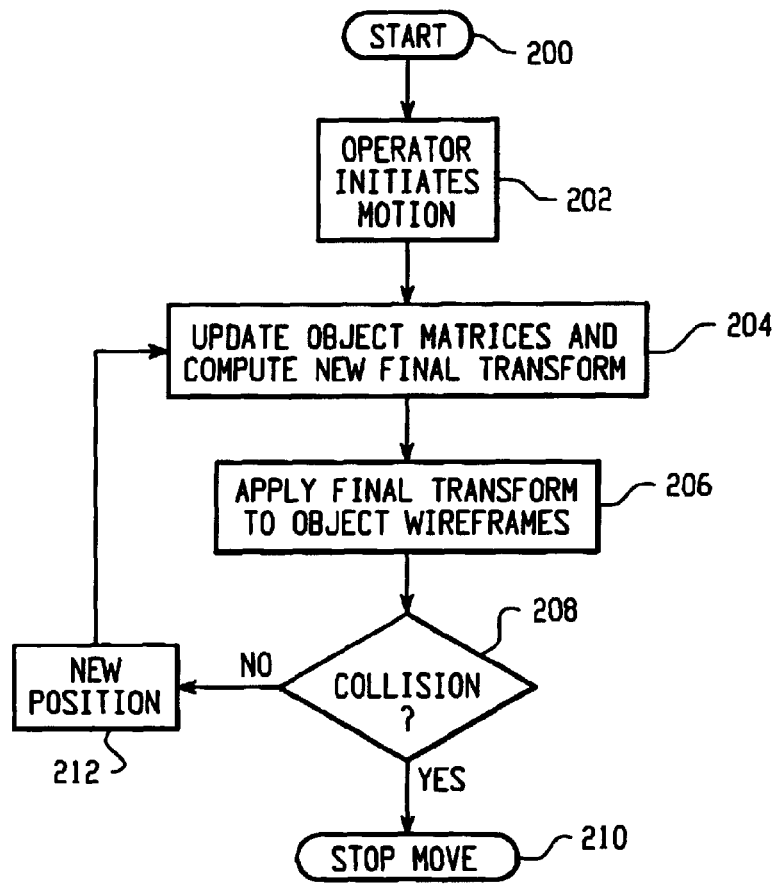
FIG. 5 is a functional flow diagram of a process implementing aspects of the present invention.

Turning now to FIG. 5, a control process in accordance with aspects of the present invention will be better appreciated. The control process begins with step 200 at power up of the imaging system. In step 200, all internal states in the control and image processing system 104 are set to initial values. The process proceeds to step 202 where a move is initiated by the operator through the operator interface 108. When the actuator (motor) sensors detect system motion from the operator initiated move, sensor signals are sent to the controller and the process moves to step 204. In step 204. system begins to gather all position and motion information from the actuating devices connected to the links of the gantry system. Each object queries the relevant actuators for necessary information to update its respective intermediate matrices. Upon accumulation of necessary information to update of the matrices, the new final transform for the objects are computed. The new final transform is computed to include a future position at the end of a predetermined time interval, for example a 0.5 second lookahead position. Next, in step 206, the new final transforms for the objects are applied to position update the wireframes of the objects and provide the new object position. The updated new object positions of the wireframe are provided to the collision detect 136 where, in step 208, the V-Collide/RAPID collision avoidance algorithms are executed. If it is determined that a collision is pending, the collision detect 136 provides the collision handling function 138 with an appropriate signal and the process progresses to step 210 where the collision handling function 138 instructs the system controller 122 of the collision. The system controller 122 provides an appropriate control signal to the gantry drive controller 120 to stop the move.

If the determination in step 208 is that there is no pending collision, the process moves to step 212 and allows the move. After step 222, the process returns to step 204 where the next position is sensed and the process repeats to be evaluated for potential collision.

Figure 6:
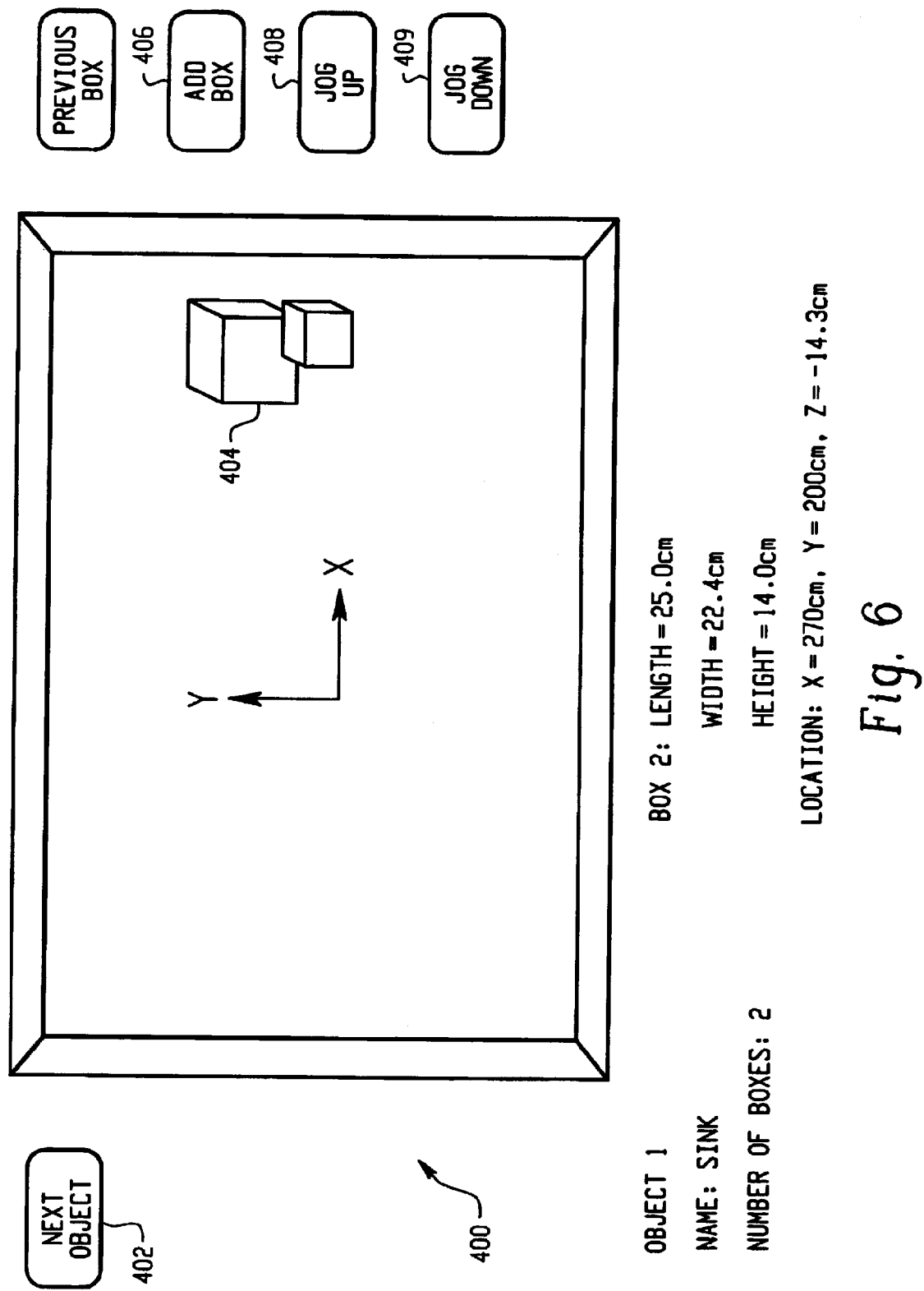
FIG. 6 is a representation of a user interface for use with aspects of the present invention.
Figure 7:
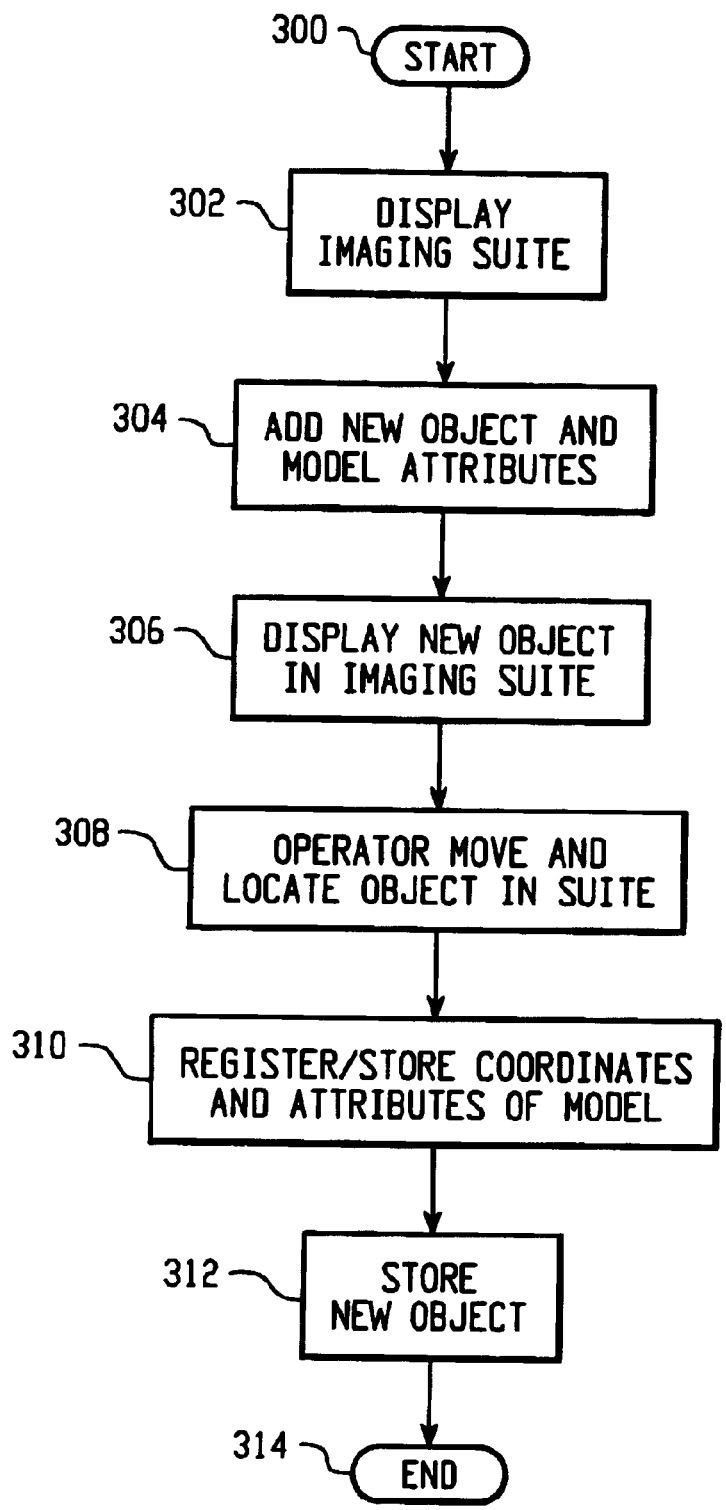
FIG. 7 is a functional flow diagram of a process in accordance with principles of the present invention.

Turning now to FIGS. 6 and 7, a process for adding new objects for collision avoidance analysis will be further appreciated. The process in FIG. 7 starts at step 300 when an operator selects an option to add a new object into the imaging suite 400 (FIG. 6). Next, in step 302, a representation of the imaging suite 400 is presented to the operator on the display 110. In step 304, the operator selects the next object input 402 to initiate the object entry dialog. For example, the new object 404 may be entered using alphanumeric or graphical interface techniques. The type of object, its dimensions and location within the imaging suite can be provided by the operator. Alternatively, an add box input 406 can result in an object being inserted in the imaging suite. After entry of the new object, the new object 404 is displayed in the imaging suite 400 in step 306. in step 308, the operator can position or modify the dimensions of the box using representative inputs 408, 409, touch screen or mouse commands. In step 310 the coordinates and attributes of the final location of the new object are determined and the process continues to step 312 where the new object is placed and processed in the model reader 130. The process ends at step 314.

While a particular feature of the invention may have been described above with respect to only one of the illustrated embodiments, such features may be combined with one or more other features of other embodiments, as may be desired and advantageous for any given particular application.

From the above description of the invention, those skilled in the art will perceive improvements, changes and modification. Such improvements, changes and modification within the skill of the art are intended to be covered by the appended claims. For example, a conventional rotary gantry gamma camera configuration can apply principles of the present invention to avoid collision between system components during operator detector positioning using the operator controls.

Having described a preferred embodiment of the invention, the following is claimed:

1. A medical diagnostic imaging system, the system comprising:
 a gantry;
 a detector support operatively connected to the gantry;
 a detector operatively connected to the detector support;
 an imaging controller controllably connected to the gantry, the detector and detector support;
 an object model reader dataset in the controller, the object model reader dataset storing as objects data related to attributes of the gantry, detector and detector support;
 a motion compute dataset defining the kinematic relationship and range of motion between the gantry, the detector support and the detector;
 objects within the range of motion of the gantry, detector and detector support as defined in the kinematic relationships, the objects modeled in the object model dataset; and
 a collision detect processor in the controller for performing real time collision analysis between objects in the model reader dataset, the collision detect processor in data communication with the controller, the object model dataset and the motion compute dataset.

2. The imaging system of claim 1 wherein the collision detect processor comprises:
 means for determining the anticipated position of objects at a predetermined time interval;
 means for constructing axis aligned bounding boxes around each model;
 means for identifying potential colliding pairs of objects from the objects in the object model reader dataset at expiration of the predetermined time interval; and
 means for performing an exact test to determine actual overlap of triangles representing objects at the expired predetermined time interval.

3. The imaging system of claim 1 wherein the attributes of the objects in the object model dataset include reference frame coordinates of vertices associated with a wire frame representation of the object.

4. The imaging system of claim 3 wherein the object model dataset includes surfaces of the object decomposed into sets of triangles related to the vertices.

5. The imaging system of claim 1 including means for updating object dataset with new objects.

6. A method of avoiding collisions with components of medical diagnostic imaging system, the method comprising the steps of:
 defining a plurality of imaging system components as wire frame representations having vertices;
 defining transform matrices for the imaging system components;

initiating movement of the imaging system components;

provide position and motion input signals for image system components in response to the movement;

updating transform matrices for imaging system components;

computing final transforms for imaging system components in response to the input signals for the imaging system components, the final transforms indicative of position of imaging system components at a predetermined time interval;

applying the final transforms to the wire frame representation generating a new position for the wire frame; and determining whether a collision is occurring between any of the plurality of imaging system components using the new wire frame positions.

7. The method of avoiding collisions with components of medical diagnostic imaging system of claim 6 including the steps of:

providing wireframe representations of objects located within an imaging suite that are within a range of motion of the imaging system components; and determining whether a collision is occurring between the objects in the imaging suite and any of the plurality of imaging system components.

8. The method of avoiding collisions with components of medical diagnostic imaging system of claim 6 wherein the step of determining whether a collision is occurring includes the steps of:

determining the anticipated position of imaging system components at a predetermined time interval;

constructing axis aligned bounding boxes around models of the imaging system components;

identifying potential colliding pairs of the imaging system components at expiration of the predetermined time interval; and performing an exact test to determine actual overlap of imaging system components at the expired predetermined time interval.

9. The method of avoiding collisions with components of medical diagnostic imaging system of claim 6 wherein the step of defining a plurality of imaging system components includes defining reference frame coordinates of vertices of the wire frame representations of the imaging system component.

10. The method of avoiding collisions with components of medical diagnostic imaging system of claim 9 wherein the step of defining a plurality of imaging system components includes the step of decomposing the wireframe representation into sets of triangles related to the vertices.

11. A medical diagnostic imaging system comprising:

a gantry;

a detector support operatively connected to the gantry;

a detector operatively connected to the detector support;

an imaging controller controllably connected to the gantry, the detector and detector support;

an object model reader dataset in the controller, the object model reader dataset storing as objects data related to attributes of the gantry, detector and detector support;

a motion compute dataset defining the kinematic relationship and range of motion between the gantry, the detector support and the detector;

an object handler dataset defining operative status of objects in the object model dataset and collision potential status between objects in the object model dataset;

objects within the range of motion of the gantry, detector and detector support as defined in the kinematic relationships, the objects modeled in the object model dataset; and a collision detect processor in the controller for performing real time collision analysis between objects in the model reader dataset, the collision detect processor in data communication with the controller, the object model dataset and the motion compute dataset.

12. The imaging system of claim 11 wherein the collision detect processor comprises:

means for determining the anticipated position of objects at a predetermined time interval;

means for constructing axis aligned bounding boxes around each model;

means for identifying potential colliding pairs of objects from the objects in the object model reader dataset at expiration of the predetermined time interval; and means for performing an exact test to determine actual overlap of triangles representing objects at the expired predetermined time interval.

13. The imaging system of claim 11 wherein the attributes of the objects in the object model dataset include reference frame coordinates of vertices associated with a wire frame representation of the object.

14. The imaging system of claim 13 wherein the object model dataset includes surfaces of the object decomposed into sets of triangles related to the vertices.

15. The imaging system of claim 11 including means for updating object dataset with new objects.

16. A medical diagnostic imaging system comprising:

a gantry;

a detector support operatively connected to the gantry;

a detector operatively connected to the detector support;

an imaging controller controllably connected to the gantry, the detector and detector support, the controller including:

means for storing as objects data related to attributes of the gantry, detector and detector support;

means for storing kinematic relationships and range of motion relationships between the gantry, the detector support and the detector;

means for defining operative status of objects and collision potential status between objects in the object model dataset; and means for performing real time collision analysis between objects.

17. The imaging system of claim 16 wherein the means for performing real time collision analysis comprises:

means for determining the anticipated position of objects at a predetermined time interval;

means for constructing axis aligned bounding boxes around each object;

means for identifying potential colliding pairs of objects from the objects at expiration of the predetermined time interval; and means for performing an exact test to determine actual overlap of triangles representing objects at the expired predetermined time interval.

* * * * *